US008500770B2

(12) United States Patent
Echevery et al.

(10) Patent No.: US 8,500,770 B2
(45) Date of Patent: *Aug. 6, 2013

(54) EXTRALUMINAL BALLOON DISSECTION

(71) Applicant: Covidien LP, Mansfield, MA (US)

(72) Inventors: Jan M. Echevery, San Jose, CA (US); Thomas Fogarty, Portola Valley, CA (US); Kenneth H. Mollenauer, Los Gatos, CA (US); George D. Hermann, Portola Valley, CA (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/669,484

(22) Filed: Nov. 6, 2012

(65) Prior Publication Data

US 2013/0060273 A1 Mar. 7, 2013

Related U.S. Application Data

(63) Continuation of application No. 13/223,856, filed on Sep. 1, 2011, now Pat. No. 8,323,304, which is a continuation of application No. 11/980,879, filed on Oct. 31, 2007, now Pat. No. 8,016,850, which is a continuation of application No. 11/273,508, filed on Nov. 14, 2005, now Pat. No. 7,314,475, which is a continuation of application No. 10/790,378, filed on Mar. 1, 2004, now Pat. No. 6,989,018, which is a continuation of application No. 10/238,108, filed on Sep. 9, 2002, now Pat. No. 6,764,497, which is a continuation of application No. 09/873,930, filed on Jun. 4, 2001, now Pat. No. 6,447,529, which is a continuation of application No. 09/039,548, filed on Mar. 16, 1998, now Pat. No. 6,013,090, which is a continuation of application No. 08/824,676, filed on Mar. 26, 1997, now Pat. No. 5,814,060, which is a continuation of application No. 08/631,221, filed on Apr. 11, 1996, now Pat. No. 5,690,668, which is a continuation-in-part of application No. 08/267,484, filed on Jun. 29, 1994, now Pat. No. 5,601,589.

(51) Int. Cl.
*A61B 17/00* (2006.01)

(52) U.S. Cl.
USPC .......................................................... 606/190

(58) Field of Classification Search
USPC ............... 604/96.01, 101.01, 101.02, 101.03, 604/101.04, 101.05, 103.05, 103.06, 103.07, 604/103.08, 103.09, 103.11, 103.12, 103.13, 604/103.14, 104, 105, 106, 107, 108, 109; 606/190, 191, 192, 194, 195
See application file for complete search history.

(56) References Cited

U.S. PATENT DOCUMENTS 4,479,497 A * 10/1984 Fogarty et al. ................. 606/194
4,526,175 A * 7/1985 Chin et al. ..................... 606/192

(Continued)

FOREIGN PATENT DOCUMENTS

WO    WO 82/00408    2/1982
WO    WO 93/24172    12/1993

OTHER PUBLICATIONS

"Endoscopic Subfascial Discission of Perforating Veins", (G. Hauer et al., Surg Endoc (1988) 2:5 12).

(Continued)

*Primary Examiner* — Ryan Severson
*Assistant Examiner* — Jonathan W Miles

(57) ABSTRACT

The present invention provides balloon dissection apparatus and methods of use in which an elongate balloon is utilized to dissect along a region that follows a naturally existing path alongside a vessel or structure, such as an artery, a vein, a lymphatic vessel, the trachea, the esophagus, or even a nerve bundle.

12 Claims, 13 Drawing Sheets

(56) References Cited

U.S. PATENT DOCUMENTS

| | | |
|---|---|---|
| 5,667,480 A | 9/1997 | Knight et al. |
| 5,690,668 A | 11/1997 | Fogarty et al. |
| 5,695,514 A | 12/1997 | Chin |
| 5,702,416 A | 12/1997 | Kieturakis et al. |
| 5,707,382 A | 1/1998 | Sierocuk et al. |
| 5,722,934 A | 3/1998 | Knight et al. |
| 5,730,756 A | 3/1998 | Kieturakis et al. |
| 5,762,604 A | 6/1998 | Kieturakis |
| 5,772,680 A | 6/1998 | Kieturakis et al. |
| 5,814,059 A | 9/1998 | Hart et al. |
| 5,814,060 A | 9/1998 | Fogarty et al. |
| 5,836,961 A | 11/1998 | Kieturakis et al. |
| RE36,043 E | 1/1999 | Knighton |
| 5,873,889 A | 2/1999 | Chin |
| 5,902,316 A | 5/1999 | Mollenauer |
| 5,968,066 A | 10/1999 | Fogarty et al. |
| 6,013,090 A | 1/2000 | Fogarty et al. |
| 6,036,714 A | 3/2000 | Chin |
| 6,102,928 A | 8/2000 | Bonutti |
| 6,152,895 A | 11/2000 | Wilk |
| 6,168,608 B1 | 1/2001 | Echeverry et al. |
| 6,312,442 B1 | 11/2001 | Kieturakis et al. |
| 6,432,121 B1 | 8/2002 | Jervis |

OTHER PUBLICATIONS

"A Quick and Atraumatic Method of Autologous Vein Harvesting Using the Subcutaneous Extraluminal Dissector", (W.R. Dimitri et al., J. Cardiovasc Surgl, 1987; 28; 103-11).

"Long Saphenous Vein Harvesting", (W. Meldrum-Hanna et al., Aust. N. Z.J. Surg 1986, 923-924).

Lam et al., "Surgical Procedure for Uncomplicated (Routine) Female Stress Incontinence", Urologic Clinics of North America, vol. 18, No. 2, May 1991.

"Vein Harvest", (Alan B. Lumaden & Felmonl Faves, III, Endoscopic Plastic Surgery (Quality Medical Publishing, Inc., 1995), pp. 535-543.

"Endoscopic Plastic Surgery", Snowden-Pencer, Inc., (1993 Brochure).

* cited by examiner

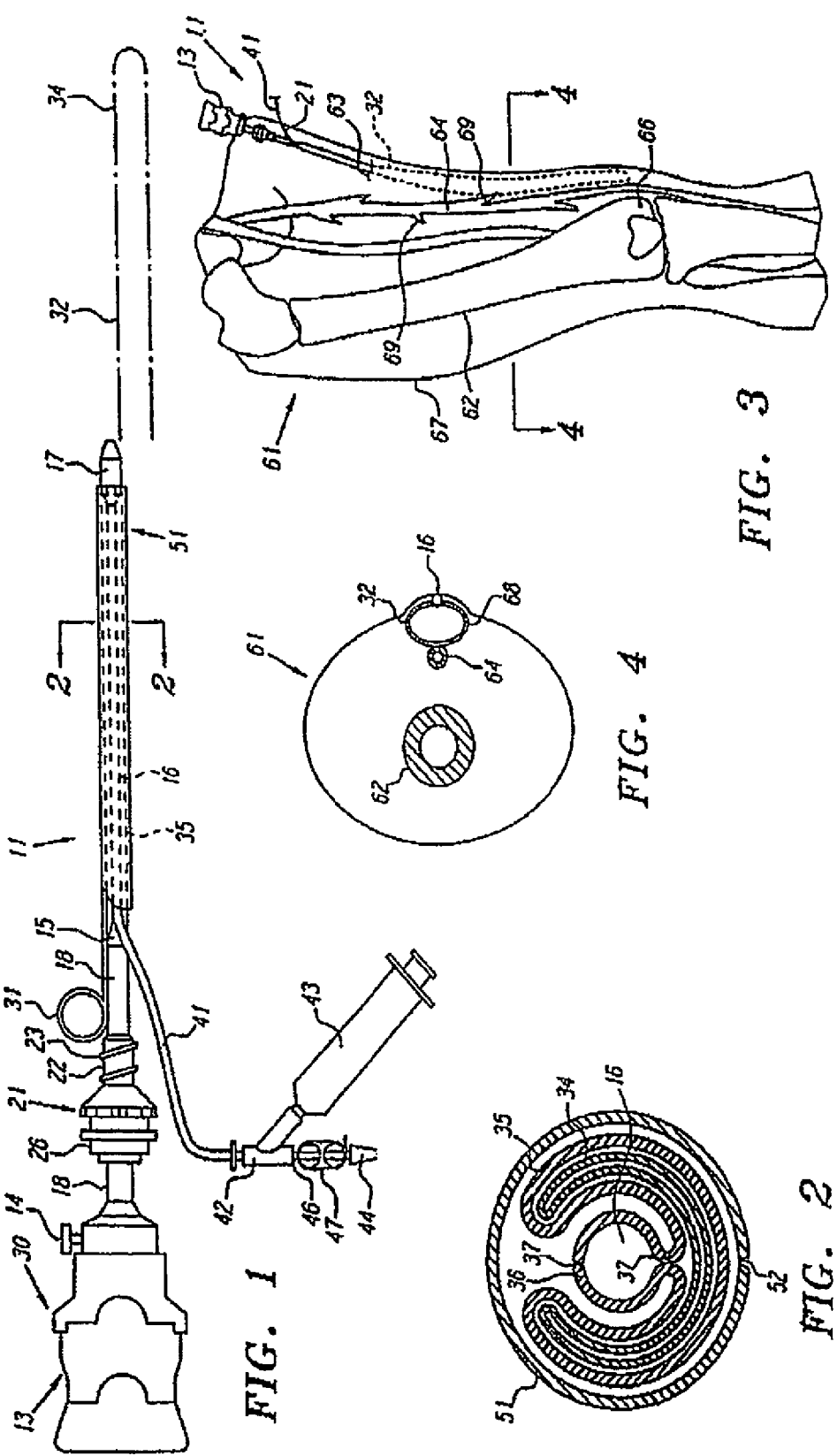

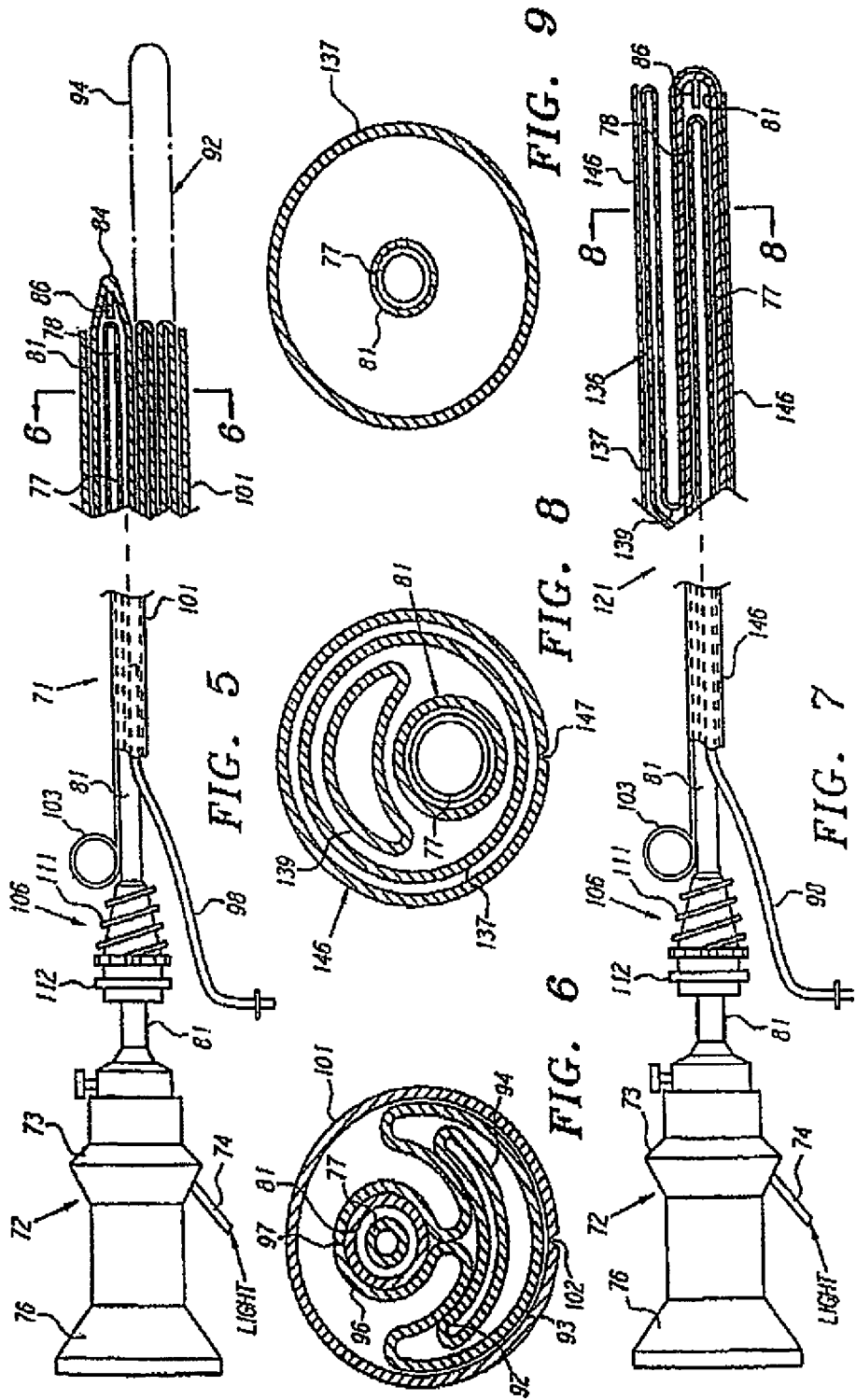

EXTRALUMINAL BALLOON DISSECTION

This application is a continuation of U.S. application Ser. No. 13/223,856, filed Sep. 1, 2011, which is a continuation of U.S. application Ser. No. 11/980,879, filed Oct. 31, 2007, now U.S. Pat. No. 8,016,850, which is a continuation of U.S. application Ser. No. 11/273,508, filed on Nov. 14, 2005, now U.S. Pat. No. 7,314,475, which is a continuation of U.S. application Ser. No. 10/790,378, filed on Mar. 1, 2004, now U.S. Pat. No. 6,989,018, which is a continuation of U.S. application Ser. No. 10/238,108, filed Sep. 9, 2002, now U.S. Pat. No. 6,764,497, which is a continuation of U.S. application Ser. No. 09/873,930, filed on Jun. 4, 2001, now U.S. Pat. No. 6,447,529, which is a continuation of U.S. application Ser. No. 09/039,548, filed on Mar. 16, 1998, now U.S. Pat. No. 6,013,090, which is a continuation of U.S. application Ser. No. 08/824,676, filed on Mar. 26, 1997, now U.S. Pat. No. 5,814,060, which is a continuation of U.S. application Ser. No. 08/631,221, filed on Apr. 11, 1996, now U.S. Pat. No. 5,690,668, which is a continuation-in-part of U.S. application Ser. No. 08/267,484, filed on Jun. 29, 1994, now U.S. Pat. No. 5,601,589, the disclosures of which are hereby incorporated by reference in their entirety.

FIELD OF THE INVENTION

The present invention relates generally to the field of extraluminal balloon dissection. More particularly, the present invention relates to vascular methods and apparatus which can used for creating an anatomic working space alongside an elongate structure, such as a vessel or nerve, for example.

BACKGROUND OF THE INVENTION

In commonly assigned copending application Ser. No. 07/893,988, filed on Jun. 2, 1992, apparatus and methods are disclosed for developing an anatomic working space for laparoscopic procedures using balloon dissection. In commonly assigned copending application Ser. No. 08/570,766, filed on Dec. 12, 1995, further improvements to the apparatus and methods disclosed in application Ser. No. 07/893,988 are disclosed. The disclosure of each of these prior applications is hereby incorporated by reference in its entirety. The apparatus and methods disclosed in the referenced prior applications include balloon dissection apparatus with relatively large surface balloons which expand laterally and are not particularly well suited for surgical procedures on elongate structures. There is therefore a need for new and improved balloon dissection apparatus and associated methods of use for dissecting or creating space alongside elongate structures in the body.

SUMMARY OF THE INVENTION

The present invention provides balloon dissection apparatus and methods of use in which an elongate balloon is utilized to dissect along a region that follows a naturally existing path alongside a vessel or structure, such as an artery, a vein, a lymphatic vessel, the trachea, the esophagus, or even a nerve bundle.

The balloon dissection apparatus for use in extraluminal balloon dissection as described herein may utilize an elongate balloon with a tunneling shaft assembly of the types described in any one of copending U.S. application Ser. Nos. 07/893,988, 08/124,283, 08/267,488, 08/388,233, 08/403,012, or 08/570,766, the disclosure of each of which is hereby incorporated by reference in its entirety. U.S. Pat. No. 4,271,839 to Fogarty et. al. which discloses a balloon catheter with an inverted balloon is also expressly incorporated by reference herein.

In a preferred embodiment, the deflated elongate balloon has at least a part of its distal extremity folded inwardly to shorten its predeployment length. The distal portion of the elongate balloon may be inverted into the proximal portion and folded inwardly to provide a balloon having a folded length of roughly one-half the length of the fully distended balloon. Additional inward folds may be provided to further shorten the balloon.

In another preferred embodiment, a thumb-shaped balloon reservoir may be provided as an integral portion of the elongate balloon. The balloon reservoir generally remains outside the body and serves to store the distal portion of the inverted, folded balloon prior to deployment. By storing the bulk of the deflated balloon outside of the body in the reservoir a longer balloon can be utilized. Provision is made for laparoscopic observation.

A bi-directionally expanding balloon is also disclosed which is useful when anatomical obstructions would cause a balloon expanding in one direction only to be blocked. The bi-directional balloon may be utilized either with or without the aid of laparoscopic observation.

In a preferred method of performing extraluminal balloon dissection, a deflated and folded elongate balloon is inserted into an incision in the body adjacent the elongate structure aided by a laparoscope, a finger, or other tunneling member. The folded elongate balloon is then optionally bluntly advanced alongside the elongate structure until a region where it is desired to perform balloon dissection is reached. As the balloon is advanced alongside the elongate structure a laparoscope may be utilized to observe beyond the distal end of the balloon, either from within or alongside the balloon. An inflation medium is then introduced into the balloon to cause the balloon to evert and propagate distally alongside the elongate structure to dissect the structure along a natural tissue plane. The laparoscope may also be use to observe dissection as the balloon propagates alongside the structure if provided. After the structure has been dissected the balloon may be deflated and withdrawn through the incision. The anatomic operating space alongside the vessel created by the dissecting balloon may be insufflated and a surgical procedure performed.

BRIEF DESCRIPTION OF THE DRAWINGS

Reference is made to the accompanying drawings, where like reference numerals are used on like parts and where illustrative embodiments of the invention are shown from which one of ordinary skill in the art will appreciate novel features and advantages of the present invention.

In the drawings:

FIG. 1 is a side elevational view of an extraluminal balloon dissection apparatus incorporating aspects of the present invention.

FIG. 2 is a cross-sectional view taken along line 2-2 in FIG. 1.

FIG. 3 is a view of the human leg illustrating the present invention being used to create an anatomic working space alongside a saphenous vein during a saphenous vein bypass procedure.

FIG. 4 is a cross sectional view taken along line 4-4 in FIG. 3.

FIG. 5 is a side elevational view of another embodiment of an extraluminal balloon dissection apparatus according to the present invention.

FIG. 6 is a cross sectional view taken along lines 6-6 in FIG. 5.

FIG. 7 is a side elevational view of yet another embodiment of an apparatus according to the present invention.

FIG. 8 is a cross sectional view taken along line 8-8 in FIG. 7.

FIG. 9 is a cross sectional view showing the balloon of FIG. 8 after it has been inflated.

DETAILED DESCRIPTION OF A PREFERRED EMBODIMENT

Figure 10:
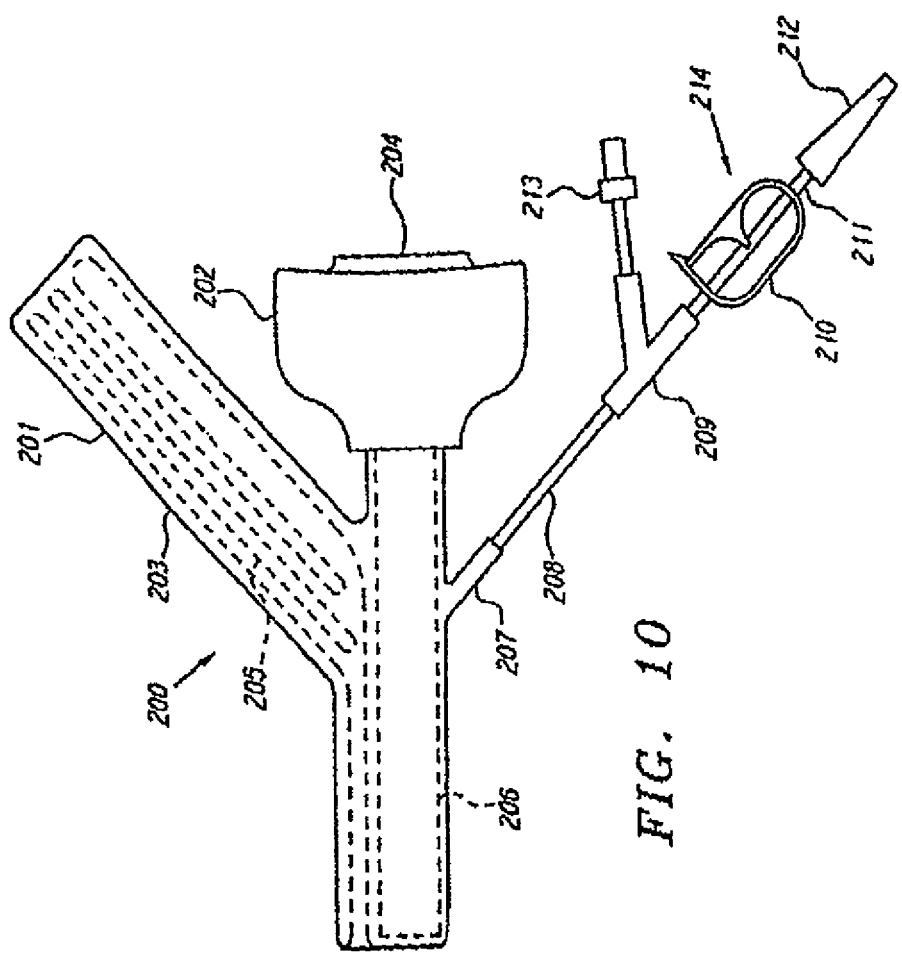
FIG. 10 is a plan view of another embodiment of an extraluminal balloon dissection apparatus according to the invention illustrating the folding and storage of the elongate balloon within a thumb-shaped balloon reservoir.

In the exemplary embodiment illustrated in FIG. 1, an extraluminal balloon dissection apparatus 11 includes a tunneling shaft assembly 30 substantially similar to the tunneling shaft assembly disclosed in application Ser. No. 07/893,988, an elongate balloon 32, a skin seal 21, and a removable balloon cover 51. The tunneling shaft assembly 30 has a three-piece handle 13. Alternatively, a hollow tube having either a one or two piece handle construction as disclosed in Ser. No. 08/570,766 may be utilized with an elongate balloon according to the invention. The three-piece handle 13 includes a cannula 18, an obturator 15, and a tunneling shaft 16, each of which extend from a different section of the handle 13. The tunneling shaft 16 extends through a bore in the obturator 15, and the obturator 15 extends through the cannula 18. The tunneling shaft 16 may have an olive-shaped, or other blunt shaped obturator 17 mounted on its distal end to provide a blunt distal end for tunneling. A skin seal 21 substantially as described in Ser. No. 08/124,283 may be utilized if needed for the procedure to be performed, in which case, the skin seal 21 is slidably mounted and frictionally retained on the outer surface of the cannula 18. A moveable collar 26 on the skin seal 21 provides for adjustment on and locking to the outer surface of the cannula 18. The outer surface 22 of the skin seal 21 is progressively cylindrical and tapered and provided with helical screw threads 23 for engaging the skin of the patient to form a seal therewith.

As shown in FIGS. 1 and 2, an elongate balloon 32 is mounted on the tunneling shaft 16 which is part of the tunneling shaft assembly 30. The elongate balloon 32, which may be described as having hot dog shape, is generally cylindrical and has a distal end 34 which extends substantially beyond the distal most point of the tunneling shaft 16 when fully inflated, as shown by the dashed extension lines in FIG. 1. The elongate balloon 32 is preferably formed from a non-elastic material so that its expansion envelope can be fairly well regulated as is known to those of skill in the art. The balloon cover 51, which may be formed integrally with the balloon 32 as disclosed in copending application Ser. No. 08/570,766, for example, or as a separable component as illustrated in FIG. 1, encloses the deflated balloon 32 and holds it against the tunneling shaft 16.

Prior to use, the distal portion 34 of the deflated balloon 32 is folded inwardly to shorten its length so that the distal portion 34 of the folded balloon 32 does not extend substantially beyond the distal extremity of the tunneling shaft 16. The distal portion 34 of the balloon 32 can be folded inwardly by inverting the distal portion 34 of the balloon 32 into the proximal portion 35 so that approximately one-half of the length of the balloon 32 is folded into the other half of the balloon 32. This reduces the overall length of the deflated balloon 32 to approximately one-half of its fully extended length. If a shorter folded balloon 32 is necessary for the particular procedure contemplated, it is possible to farther shorten the balloon 32 by again folding the distal most portion of the balloon 32 inwardly so that the deflated balloon 32 is now only approximately one-fourth of its fully extended length.

In the embodiment shown in FIGS. 1 through 4, die balloon 32 is releasably secured to the tunneling shaft 16 by a sleeve 36, as best shown in FIG. 2. The sleeve 36 can be formed from the same material as the balloon 32 and may be formed as an integral part of the balloon 32 by bonding the balloon material together as shown at reference numeral 37 in FIG. 2. Alternatively, the sleeve 36 may be formed as a separate member of the balloon 32 and bonded to the balloon 32 by welding, heat sealing, or through the use of a suitable adhesive, for example. The sleeve 36 extends substantially along the entire length of the balloon 32 and circumscribes the tunneling shaft 16. The sleeve 36 is preferably provided with a weakened region 37 extending the length thereof which can be formed in a suitable manner, such as by providing axial perforations extending along the length of the sleeve 36. The weakened region 37 permits the sleeve 36 to be separated from the tunneling shaft 16 when it is desired to separate the balloon 32 from the tunneling shaft 16, as will be described below.

In order to inflate the balloon 32, a flexible tubular member 41 may be utilized as an inflation lumen for the balloon 32. The distal extremity of the tubular member 41 is inserted into the balloon 32 so that the lumen in the tubular member 41 opens into the interior space of the balloon 32. A wye adaptor 42 is secured to the proximal extremity of the tubular member 41. A hand operated syringe 43 may be corrected to the wye adaptor 42 as shown in FIG. 1 and utilized to inflate the balloon 32 with a suitable fluid, such as saline solution, for example. The wye adaptor 42 is also connected to another fitting 44 by tube 46 which has a pinch clamp 47 mounted thereon. A male evacuation fitting 44 terminated the tube 46 and may be connected to wall suction to evacuate the balloon 32 after the balloon 32 has been deployed to dissect as will be described below.

In FIGS. 1 through 4, a removable balloon cover 51 of the type described in copending application Ser. Nos. 07/893,988 or 08/124,283 may be utilized in connection with the extraluminal balloon dissection apparatus 11 disclosed herein. The removable balloon cover 51 serves to frictionally retain the collapsed balloon 32 relative to the tunneling shaft 16. The removable balloon cover 51 preferably has a weakened region 52 (see FIG. 2) extending along the length thereof to permit the balloon cover 51 to be separated from the balloon 32 and the tunneling shaft 16 when it is desired to inflate the balloon 32. An integral balloon cover of the type described in Ser. No. 08/267,438, for example, may be utilized with the balloon dissection apparatus 11 in lieu of the removable cover 51. Such an integral balloon cover may be provided with a weakened region extending along its length so that the balloon cover separated from the balloon 32 and the tunneling shaft 16 as the balloon 32 is inflated. Alternatively, the balloon 32 can be packed into the balloon cover 51 without a guide shaft 16.

Turning now to FIGS. 3 and 4, operation and use of the extraluminal balloon dissection apparatus 11 will now be described in connection with an exemplary balloon dissection procedure. One example of a procedure where the present balloon dissection apparatus 11 may be used is saphenous vein bypass procedure where it is desired to improve the circulation of arterial blood in the leg 61 of a patient having a diseased artery in the leg 61. As shown in FIG. 3, to perform this procedure, an incision 63 is made through the skin 67 in the leg 61 immediately adjacent the saphenous vein 64 selected to serve as the bypass. The distal extremity defined by the olive-shaped tip 17 of the balloon dissection apparatus 11 is then introduced through the incision 63 and advanced along the saphenous vein 64 between the vein 64 and the skin 67 until the tunneling shaft 16 and folded balloon 32 are disposed within the leg 61 adjacent the saphenous vein 64. It should be appreciated that, if desired, dissection can be accomplished along the saphenous vein 64 on the side of the vein 64 away from the skin 67.

When the tunneling shaft 16 and folded balloon 32 are in the proper position adjacent the saphenous vein 64, the balloon cover 51 is removed, either by physically removing the balloon cover 51 (facilitated by finger ring 31) and withdrawing the cover 51 from the incision or, alternatively, in the case where an integral balloon cover is utilized, by merely inflating the balloon 32 which causes the integral cover to separate. Once the balloon cover 51 has either been removed (or separated by inflation of the balloon in the case of an integral cover), the balloon 32 is progressively inflated by introducing a fluid, such as saline solution, for example, through the syringe 43 into the interior space of the balloon 32. As the balloon 32 begins to inflate, the distal portion 34 of the balloon 32 begins to unroll, everting outwardly and propagating in a distal direction downwardly in the leg 61 toward and beyond the knee 66 until the distal portion 34 of the balloon 32 is fully extended, as shown by the dashed line in FIG. 3. The saphenous vein 64 is dissected from adjacent tissue along its length as the balloon 32 progressively expands and forms a tunnel alongside the vein 64. Dissection follows a natural tissue plane immediately adjacent the vessel or elongate structure. The dissecting balloon 32 propagates along the vessel following a natural tissue separation plane between the vessel and surrounding tissue. Thus, dissection occurs as the balloon 32 progressively inflates and follows the desired natural separation plane alongside the vessel.

After the balloon 32 has been completely inflated and has extended alongside the vein 64 causing the vein 64 to be dissected from adjacent tissue, the balloon 32 is deflated by opening the clamp 47 and applying suction to fitting 44. After deflation, the balloon 32 may be withdrawn through the incision 63 by pulling on the tubular member 41 to cause the releasable balloon 32 to be separated from the tunneling shaft 16 along the weakened region 37 of the sleeve 36. The skin seal 21 is then optionally advanced and threaded into the incision 63 to form a gas-tight seal with the skin 67 if it is desired to insufflate the dissected space alongside the saphenous vein 64. An insufflation gas may be introduced through the fitting 14 on the handle 13 into the dissected space between the saphenous vein 64 and the skin 67 to provide an anatomic walking space (68 in FIG. 4) extending lengthwise along the saphenous vein 64. The entire tunneling shaft assembly 30 can then be removed from the incision 63, leaving the skin seal 21 and cannula 18 in place to maintain a gas-tight seal with the leg 61. The cannula 18 may be provided with a duckbill or flapper valve (not shown) to prevent the insufflation gas from escaping through the cannula 18 after withdrawal of the tunneling shaft assembly 30.

The saphenous vein 64 has side branches 69 which are exposed within or adjacent to the insufflated anatomic space 68 extending along saphenous vein 64. Clips (not shown) can be applied to the aide branches 69 in several ways. For example, an incision can be made at the distal extremity of the insufflated space 68 by the use of a trocar, for example, and a clip applier can be introduced through the trocar and hemostats or clips can be applied to the side branches 69. In order to facilitate this aspect of the procedure, a laparoscope may be introduced through the skin seal 21 to permit the placement of the caps to be observed. In this manner, many of the side branches 69 can be clipped utilizing only one incision in the groin and another incision below the knee 66. Thus, the procedure of the present invention greatly reduces the number of incisions required to clip the side branches 69 of the saphenous vein 64 over traditional open bypass procedures.

Another method of clipping the side branches 69 involves the use of an operating endoscope which may be introduced through the skin seal 21. The operating endoscope has an instrument channel through which a clip appplier can be introduced into the dissected space adjacent the saphenous vein 68 to clip off the side branches 69 while the procedure is being viewed through the endoscope.

If it is desired to advance still further down the leg 68 than can be accomplished with the first balloon dissection apparatus 11, a second similar balloon dissection apparatus 11 can be introduced through a second incision lower down the leg and the same procedure utilized to dissect the saphenous vein 64 down to the ankle of the patient. The same procedure as described above can be utilized to clip off the side branches 69 of that portion of the saphenous vein 64 that is dissected by use of the second apparatus 11. After clipping of the side branches 69 has been completed, valves within the saphenous vein 64 can be removed in a conventional manner if that is desired. To perform the arterial bypass procedure, the upper portion of the saphenous vein 64 can then be connected through the first incision to the artery it is desired to bypass and reconnected through the lower incision. The incisions may be closed in a conventional manner.

By utilizing a balloon dissection apparatus of the present invention, it is possible to provide working access to the saphenous vein 64 through only moderate sized incisions made at me top and bottom of the leg 61 and possibly one additional incision in the middle of the leg 61. Thus, use of an extraluminal balloon dissection apparatus eliminates many of the incisions in the leg 61 which previously been required in order to clip off or occlude the side branches 69 of the saphenous vein 64. The reduced number and length of incisions greatly reduces the risk of infections from multiple and large surface area incisions. From a patient standpoint, the pain and recovery time in the hospital are greatly reduced over traditional procedures.

Balloon dissection apparatus as disclosed herein can also be used for harvesting the saphenous vein for use in a coronary artery bypass procedure, for example. In the past, it has been necessary to make a full length incision all the way down the leg 61 of the patient to remove the saphenous vein 64 for the bypass procedure. With a balloon dissection apparatus of the present invention, it is possible to make a single incision in the groin in the patient and then utilize the balloon dissection apparatus to create an anatomic working space adjacent the saphenous vein 64 in the leg 61 through balloon dissection. This can be accomplished by introducing an extraluminal balloon dissection apparatus 11 alongside the saphenous vein 64 and thereafter inflating the balloon 32 to cause it to evert outwardly and propagate down the leg, in the process dissecting tissue away from the saphenous vein 64 along substantially the entire length of the saphenous vein 64 to create an anatomic working apace, as previously described. In this procedure the inflation pressures for the balloon 32 are generally below one atmosphere.

After dissection has occurred, the balloon 32 is removed, and the anatomic working space 68 created by balloon dissection is then insufflated and additional trocars, as needed, are inserted into the insufflated dissected space 68. Side branches 69 of the saphenous vein 64 may be exposed by additional manual dissection and are clipped and transected. The saphenous vein 64 is then dissected free from its surrounding tissue bed and the proximal and distal ends of the vein 64 are clipped and transected to allow the saphenous vein 64 to be removed or harvested through the incision 63. This approach drastically reduces the length of the incision 63 which is normally required to harvest the saphenous vein 64. The saphenous vein 64 can be pulled out through the incision 63 and the side branches 69 can be closed on the operating table in a standard procedure. Similarly, as previously described, valves within the saphenous vein 64 can be removed or disabled in a conventional fashion if need be.

In connection with the present invention, it has been found preferable to utilize a nonelastomeric balloon 32 so that it is possible to control the shape of the dissected region. By way of example, for extraluminal procedures involving the saphenous vein, it is desirable to have a tunneling shaft 16 with a length of approximately 12 inches and a fully distended balloon 32 having a axial length of 20 to 30 inches and a maximum diameter when inflated of approximately 1 to 3 inches. It should be appreciated that different sizes of balloons can be provided in accordance with the present invention to provide inflated diameters as great as 3 to 4 inches where that may be necessary or desirable. Alternatively, the extraluminal dissection balloons can be of a relatively small diameter, such as 10 millimeters, for example, when it is desired to tunnel down along the natural plane of an artery for the purpose of inserting a synthetic graft, for example.

In place of a rigid tunneling shaft assembly 30, it should be appreciated that a semi-rigid tunneling assembly could be provided to give some flexibility, yet enough rigidity to make blunt dissection possible to facilitate the advancement of the balloon 32 to a desired location alongside the vessel of interest. It should also be appreciated that such a balloon dissection apparatus 11 could be utilized in conjunction with other vessels in the human body, as well as with other elongate structures such as the esophagus, carotid arteries, brain drain shunts, and nerves.

Another embodiment of an extraluminal balloon dissection apparatus 71, according to the invention, is shown in FIGS. 5 and 6. In this embodiment, the apparatus 71 includes a conventional endoscope 72 which has a housing 73, a light inlet fitting 74 mounted on the housing 73, and an eye piece 76. The laparoscope 72 has a probe 77 extending from the housing 73. An objective lens (not shown) mounted in the distal extremity 78 of the probe 77 may provide a suitable viewing angle, such as a straight viewing angle parallel to the longitudinal axis of probe 77 or angle of 30 degrees with respect to the longitudinal axis, for example. As is well known to those of the skill in the art, the laparoscope 72 is provided with optics for receiving a light source at the fitting 74 and directing the light out the distal extremity 78 of the probe 77 so that light is supplied beyond the distal end 78 of the probe 77. This permits the surgeon to observe beyond the distal end 78 of the probe 77 through the eyepiece 76 or on a video monitor, if the laparoscope utilized is capable of providing a video output.

The balloon dissection apparatus 71 may utilize, as a tunneling member, an elongate tubular member 81. The tubular member 81, to addition to serving as a scope cover for the laparoscope 72, also serves as a tunneling member to permit the apparatus 71 to be advanced bluntly alongside the saphenous vein, following a natural dissection plane adjacent the vein. The tabular member 81 can be of the type described in copending application Ser. No. 08/267,488 and is preferably formed of a suitable transparent material, such as a clear polycarbonate. The tabular member 81 has a bore extending therethrough which is sized to that it can readily accommodate the probe 77 of the laparoscope 72. The tubular member 81 may have sufficient length to accept the entire length of the probe 77. The tabular member 81 has a rounded, substantially hemispherical tip 84 at its distal extremity which can be formed integrally therewith as shown, or alternatively, as a separate piece and bonded to the tubular member 81 by the use of a suitable adhesive, for example. The tubular member 81 may also have an open, yet blunt, distal extremity as disclosed in copending application Ser. No. 08/570,766, to permit observation through the laparoscope 72 through the open distal end. When a closed, rounded tip 84 is utilized as shown in FIG. 5, the tip 84 is preferably formed from a transparent material such as a clear polycarbonate, to facilitate observation through the distal end 84.

To further facilitate observation through a closed distal end, a baffle 86 may be mounted in the bore of the tubular member 81 and extends laterally and axially thereof. The baffle 86 can be formed integrally with the distal end 84 or, alternatively, can be formed of a separate material which is then bonded to the distal end 84 by a suitable adhesive. Assuming that the laparoscope 72 is of a type in which the light transmitting capabilities are provided in one semi-circular region of the probe 77, and viewing capabilities are provided through the other semi-circular region, the baffle 86 is positioned in such a manner so that it will inhibit, if not prevent, light emitted from the distal extremity 78 of the probe from bouncing off the inner surface of the distal end 84 and creating a glare which may obscure vision through the eye piece 76. In order to prevent such a glare, the baffle 86 is preferably formed of an opaque material, such as a black opaque material for example. Alternatively, the baffle 86 may be provided with one surface which is opaque so that light cannot be transmitted through the baffle 86 to the lower half of the probe 77 making a clear field of vision possible through the tubular member 81.

An elongate balloon 92 similar to the balloon 32 in the previous embodiment may be utilized with the apparatus 71. The balloon 93 has proximal and distal extremities 93 and 94, respectively. (See FIG. 6). As in the previous embodiment, the distal extremity 94 may be folded inwardly into the interior of the balloon 92 to reduce the overall balloon length by approximately one-half. As previously described, the balloon 92 may have its overall length reduced even farmer by additional inward folding. Ah shown in FIG. 6, the balloon 92 has a sleeve 96 extending axially thereof for at least a portion of its length. The sleeve 96 surrounds the tubular member 81 and secures the balloon 92 to the tubular member 81. The sleeve 96 is provided with a weakened region 97 extending the length thereof to permit the balloon 92 to be removed from the tubular member 81. A tubular member 98 of the type previously described extends into the interior space of the balloon 92 and may be connected to a suitable inflation source, such as a syringe, for example, to communicate fluid through its internal lumen into the balloon 92.

As in the previous embodiment, a removable balloon cover 101 may be utilized in connection with the apparatus 71. Alternatively, an integral balloon cover, as previously described, may also be used. The balloon cover 101 surrounds the folded balloon 92 and retains the balloon 92 in close proximity to the tubular member 81 prior to removal of the cover 101 and deployment of the balloon 92. The balloon cover 101 has a weakened region 102 (see FIG. 6) extending the length thereof and may be provided with a finger ring 103 to facilitate removal of foe cover 101, as previously described.

A skin seal 106 of the type previously described may also be utilized in connection with the apparatus 71. The skin seal has a conical surface which is provided with a continuous helical thread 111. An axially movable collar 112 is mounted on the skin seal 106 and is moveable to releasably clamp the skin seal to the scope cover 81.

Operation and use of the extraluminal balloon dissection apparatus 71 is very similar to that of the balloon dissection apparatus 11 previously described. The principal difference in the this embodiment is that a laparoscope 72 is continuously available during the introduction of the apparatus 71 into an incision and during advancement of the apparatus 71 alongside the elongate structure or vessel to be dissected free of adjacent tissue. As before, the apparatus 71 can be tunneled alongside the saphenous vein, either on the side of the saphenous vein adjacent the skin, or on the side away from the skin. The balloon 92 is then initiated to dissect the vein away from adjacent tissue beyond the distal end 84 of the tubular member 81. It has been found preferable to dissect alongside the saphenous vein on the side of the leg away from the skin. By utilizing this approach, the light from the laparoscope 72 makes it possible to visually identify the saphenous vein location and side branches by forming a silhouette on the skin. This makes it possible to locate further necessary incisions and minimize their size.

After the balloon 92 has been disposed adjacent the saphenous vein or other elongate structure, the cover 101 is removed from the folded balloon 92 and tubular member 81, by separation along its weakened region 102. Removal of the cover 101 is facilitated by finger ring 103. The balloon 92 is then inflated, and the balloon 92 unrolls and everts in a distal direction to dissect the saphenous vein from adjacent tissue beyond the distal end 84 of the tubular member 81. (If an integral cover is utilized in lieu of the hard cover 101, the integral cover ruptures along its weakened region during inflation thereby releasing the balloon 92). The balloon 92 can be viewed through the laparoscope 72 as it unrolls through the laparoscope 72. After the balloon 92 is completely distended and inflated, it can be deflated as previously described and stripped off the tubular member 81 along the weakened region 97, and withdrawn through the incision. Thereafter, the skin seal 106 may be threaded into the incision to provide a substantially gas-tight seal therewith if a gas-tight operating space is desire. The laparoscope 72 and tubular member 81 can then be removed from the skin seal 106 and a cannula having an insufflation capability can be introduced through the skin seal 106 to insufflate the dissected anatomic working space adjacent the vessel. Alternatively, another incision can be made and the desired surgical procedure can be performed through the other incision while viewing through the laparoscope 72 already inserted in the first incision. Thus, the balloon dissection apparatus 71 offers the advantages obtained with the balloon dissection apparatus 11 previously described, while at the same time making it possible to view blunt dissection as it occurs adjacent the saphenous vein or other elongate structure.

Referring now to FIGS. 7 through 9, another embodiment of a balloon dissection apparatus 121 according to the present invention is illustrated. The apparatus 121 is substantially similar to the apparatus 71 of the previous embodiment, the difference being that the tubular member 81 is inserted into (rather than being disposed alongside) the elongate balloon 136. As in the previous embodiment, the tubular member 81 receives a conventional laparoscope 72 and serves the dual function of a scope cover and blunt tunneling member.

As shown in FIG. 7, the tubular member 81 is inserted inside the inverted and folded elongate balloon 136 between one of the inwardly folded layers of the balloon 136 and an outer, proximal balloon layer. The elongate balloon 136 may have its proximal end 137 secured to the tabular member 81 in a fluid-tight manner, such as by gluing or other bonding techniques. Alternatively, the elongate balloon 136 may be completely sealed, and the tubular member 81 inserted into the proximal end of the elongate balloon 136, inverting the sealed balloon 136 inwardly as the tubular member 81 is advanced toward the distal most portion of the balloon 136, as disposed in application Ser. No. 08/570,766.

In the exemplary embodiment of FIG. 7, the distal portion 139 of the balloon 136 is inverted and folded into the proximal portion 137 of the balloon 136 such that the distal half of the balloon 136 resides within the proximal half, as previously described. The tubular member 81 is inserted through the open proximal end of the balloon 136 and advanced between the balloon layers defining the proximal and distal halves of the balloon 136 and advanced between the is adjacent the approximate midpoint, now distal, fold in the balloon 136. Because the tubular member 81 and hence, the laparoscope 72, are within the interior space of the balloon 136, the balloon 136 is preferably formed from a substantially transparent material so that laparoscopic observation is still possible. In this case, observation occurs through the distal extremity of the tubular member 81 and the folded balloon 136. An opaque baffle 86, as previously described, may be utilized to minimize unwanted reflections of light into the laparoscope 72. Alternatively, a tubular member 81 having an open distal end substantially as described in copending application Ser. No. 08/570,766 may be utilized so that laparoscopic observation is through the open distal end of the tubular member 81.

A balloon cover 146, having a longitudinally extending and weakened region 147, may also be utilized in this embodiment. The balloon cover 146 serves to compress the folded collapsed balloon 136 into a more compact state and to frictionally retain the balloon 136 on the tubular member 81 during tunneling advancement of the apparatus 121. It is to be noted that an integral cover, as previously described, could be utilized in lieu of the removable balloon cover 146 in this embodiment as well.

Operation and use of the balloon dissection apparatus 121 is substantially similar to that of the previous embodiments. Because the balloon 136 and the distal extremity of the scope cover 81 are substantially transparent, observation through the laparoscope is possible during bloat tunneling and subsequent balloon dissection. After the apparatus 121 has been inserted through an incision adjacent the elongate structure to be dissected and advanced bluntly under laparoscopic observation, if desired, to the location where dissection is to be performed, the balloon cover 146 is removed and the balloon 136 is inflated through the tubular member 98. The balloon cover 146 is removed by pulling the finger ring 103 proximally to cause the balloon cover 146 to separate from the tubular balloon 136 along its weakened region 147.

As the balloon 136 is inflated, it everts and propagates following a natural separation plane alongside the elongate structure in a manner similar to the balloons previously described. The balloon 136 inflates around the tubular member 81 providing an anatomic working space adjacent the elongate structure, as shown in cross-section in FIG. 9. After the elongate structure has been dissected from adjacent tissue by the balloon 136, the balloon 136 is deflated and the apparatus 121 and laparoscope 72 are withdrawn through the incision, either serially or together. The remainder of the surgical procedure is then completed and the incision (or incisions) closed.

Figure 11:
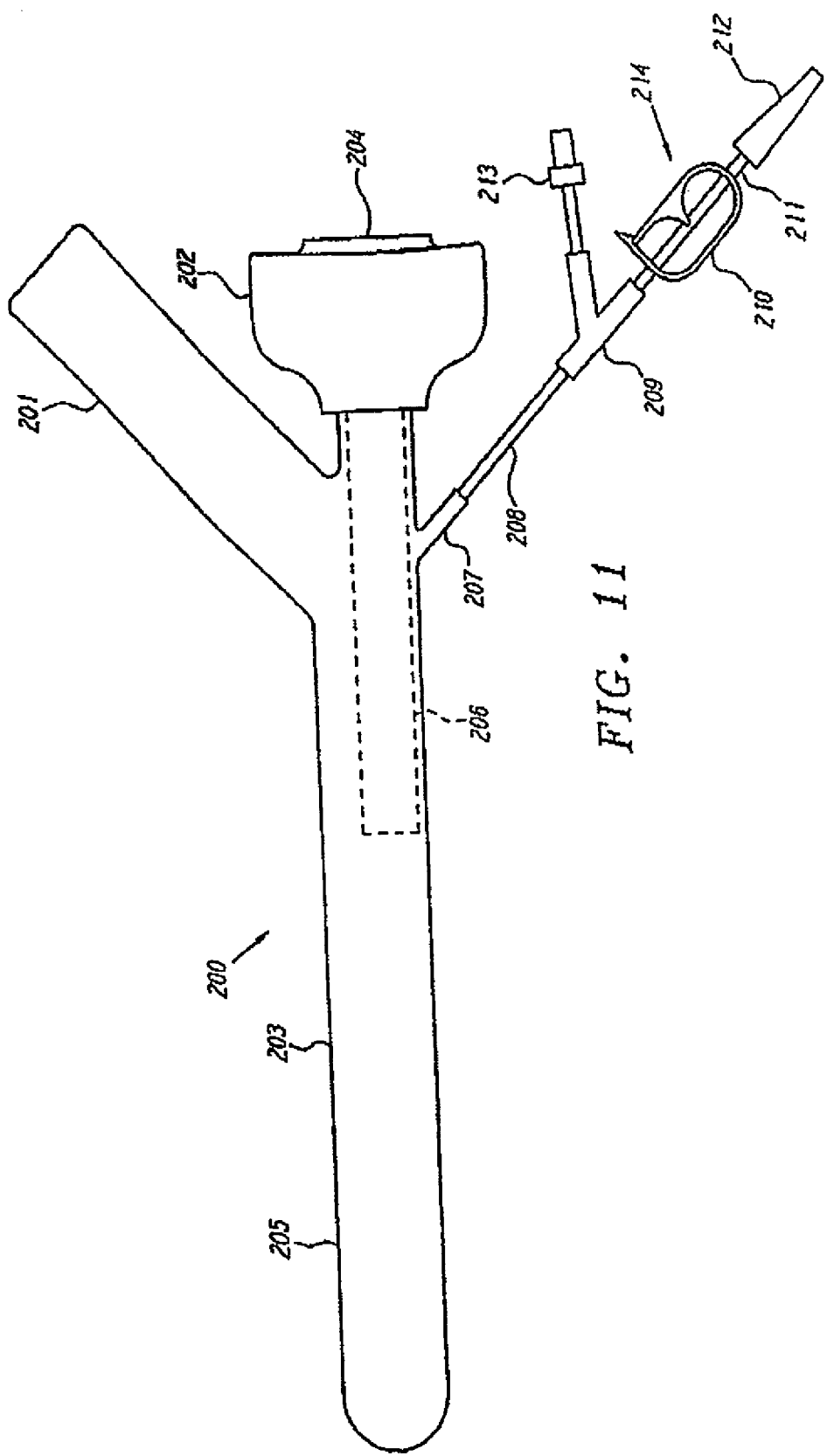
FIG. 11 is a plan view of the apparatus of FIG. 10 showing the elongate balloon fully distended after inflation.

Another embodiment of a balloon dissection apparatus 200 according to the invention is shown in FIGS. 10 and 11. The apparatus 200 is provided with a laterally extending thumb-shaped reservoir 201 which is itself part of the elongate balloon 203. A housing 202 having a tubular balloon sleeve 206 extending therefrom terminates the balloon 203 and may receive a laparoscope (not shown) if visualization is required or desirable for the procedure contemplated. An instrument seal 204, which may be of the type in copending application Ser. No. 08/570,766, is mounted in the housing 202 to provide a fluid-tight seal between the interior of the handle 202, which is in fluid communication with the interior of the balloon 202, and a laparoscope. The balloon sleeve 206 is similar to the balloon sleeve described in copending application Ser. No. 08/403,012, and may be formed integrally with the housing 202 or as a separate member.

The elongate balloon 203 is substantially similar to the balloons utilized in connection with the previous embodiments and may be inverted and folded inwardly to reduce its predeployment length in similar fashion. The proximal end of the balloon 203 is open and may be terminated in a fluid-tight manner in the housing 202, as shown, or on an outer surface of the balloon sleeve 206. The open proximal end of the balloon 203 may be secured between the interior of the housing 202 and the balloon sleeve 206 as described in application Ser. No. 08/403,012. The balloon 203 is preferably formed from a substantially transparent material to facilitate laparoscopic observation through the balloon 203 as described below.

Prior to use, the distal portion 205 of the deflated balloon 203 is inverted and folded inwardly to shorten the overall length of the balloon 203. The distal portion 205 of the inverted, folded balloon 203 is pushed into the reservoir 201, as shown in FIG. 10. Additional folds may be provided, as necessary, to further shorten the deflated balloon 203 and to make it possible to store the majority of the balloon 203 in the reservoir 201.

The reservoir 201 provides several advantages over the previous embodiments. First, the reservoir 201 allows a more compact design in that a long balloon may be folded and stored in the reservoir 201 outside the body with only a relatively short portion of the balloon 203 extending into the incision. This feature is advantageous because it allows the use of a relatively short insertion device (i.e., the balloon sleeve 206 or the distal tip of the laparoscope when the balloon sleeve 206 is not provided, as shown in later embodiments of the invention, or a finger of hand) instead of the relatively long tunneling members contemplated in the previous embodiments. In this regard, it has been found desirable to utilize the balloon 203, which follows a natural dissection plane, rather than a blunt tunneling member, which may not follow the natural plane, to perform as much of the dissection as possible. Second, because the majority of the balloon 203 is disposed outside the body, the axial length of the balloon 203 is not as constrained to the length of the tunneling member as in previous embodiments.

An inflation harness 214, also of the type previously described in Ser. No. 08/570,766, may be utilized to communicate a suitable inflation medium, such as saline solution, for example, to the interior of the balloon 203 to inflate the balloon 203. An inflation lumen 207 extends from the balloon 203 and is connected to a tubular member 208, which in turn is connected to a wye fitting 209. Wye fitting 209 may have one port connected to a luer-type fitting 213 and another port connected to another tubular member 211. A pinch clamp 210 is mounted on the tubular member 211 and is clamped off during balloon inflation and opened during deflation. A male fitting 212 terminates the tubular member 211 and is suitable for connecting to a hospital evacuation source when it is desired to deflate the balloon 203.

In a preferred method of use, a laparoscope is inserted through the instrument seal 204 and advanced through the balloon sleeve 206 until its distal end reaches the distal end of the balloon sleeve 206 and the folded balloon 203 which covers the distal end of the balloon sleeve 206. The apparatus 200 may then be inserted into the body of a patient through an incision adjacent the elongate structure to be dissected. Alternatively, the apparatus 200 may be introduced through the incision into the body without the aid of the laparoscope if observation is not required or deemed necessary. Although a laparoscope is preferably utilized with the apparatus 220, its use is optional in that the balloon sleeve 206 to the desired point adjacent the elongate member to facilitate advancement of the apparatus 200 to the desired point adjacent the elongate structure.

When a laparoscope is utilized, the apparatus 200 is advanced alongside the elongate structure using the laparoscope and/or balloon sleeve 206 as tunneling members until a desired location for balloon dissection is reached. It is to be noted that the reservoir 201 does not generally enter the incision and remains outside the body. When the desired location is reached, the balloon 203 is inflated by connecting a suitable inflation source, such as a syringe, for example, to the luer fitting 213 and introducing the inflation medium into the interior of the balloon 203. As the inflation medium is progressively introduced, the balloon 203 everts outwardly propagating alongside the elongate structure to dissect adjacent tissue away from the structure, as previously described. As the balloon 203 is inflated, the distal portion 205 of the balloon 203 stored in the reservoir 201 is gradually withdrawn from the reservoir by the distal propagation of the balloon 203. Inflation continues until the distal portion 205 of the balloon 203 is completely withdrawn from the reservoir 201 and the balloon 203 is fully distended alongside the structure. (See FIG. 11) The surgeon can observe the progress of the dissection procedure through the laparoscope from inside the balloon 203 as the balloon 203 unrolls and propagates alongside the structure.

After an operating space adjacent the vessel or structure has been created by dissection, the elongate balloon 203 is deflated by opening the pinch clamp 210 and withdrawing the fluid from the balloon 203 through the male fitting 212. The laparoscope and apparatus 200 may then be withdrawn from the incision and additional cannulas or other laparoscopic instruments, as contemplated by the particular procedure being performed, may be inserted through the incision into the dissected operating space and the procedure completed.

Figure 12:
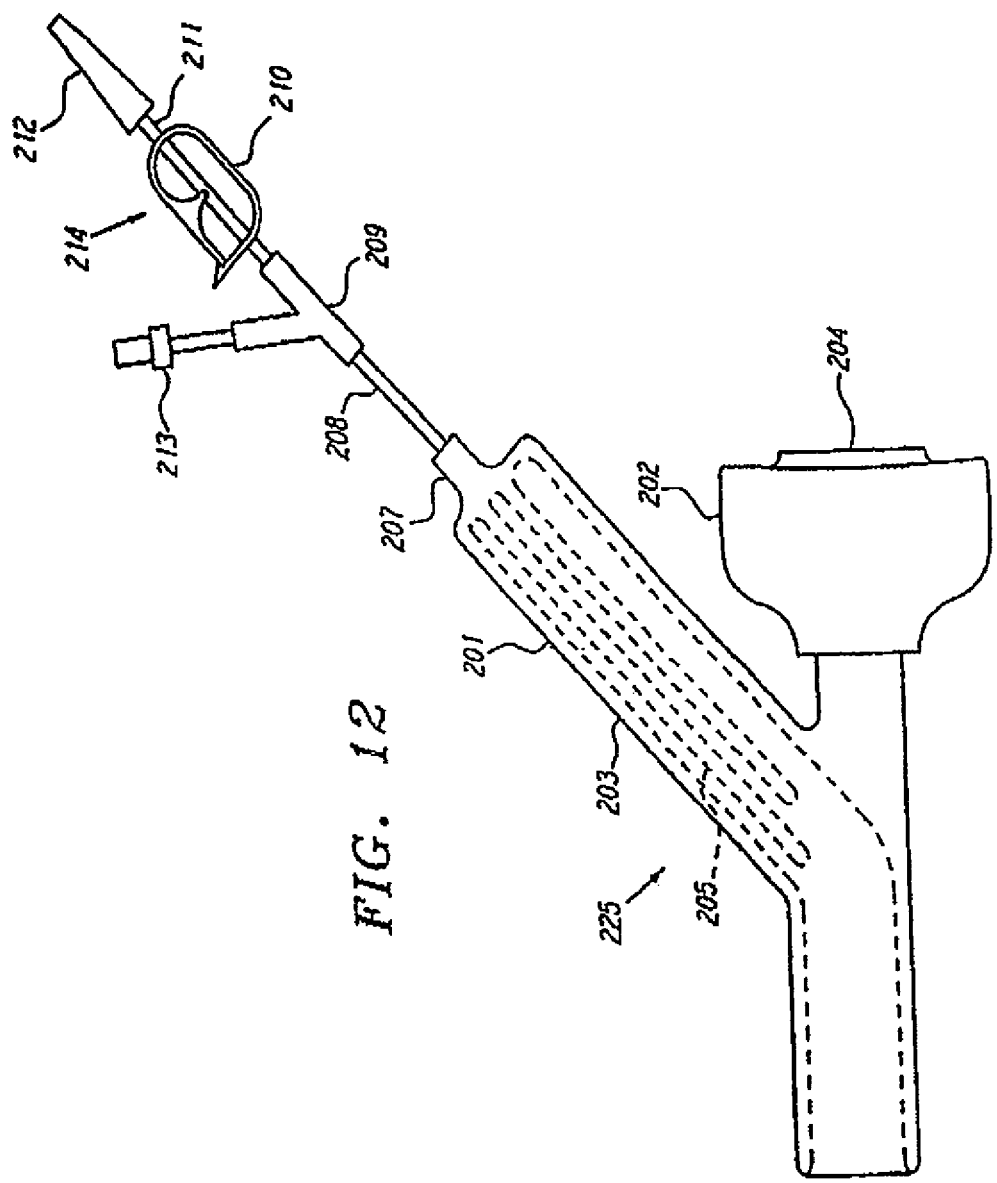
FIG. 12 is plan view of another embodiment of an extraluminal balloon dissection apparatus according to the invention utilizing an elongate balloon and a thumb-shaped balloon reservoir.
Figure 13:
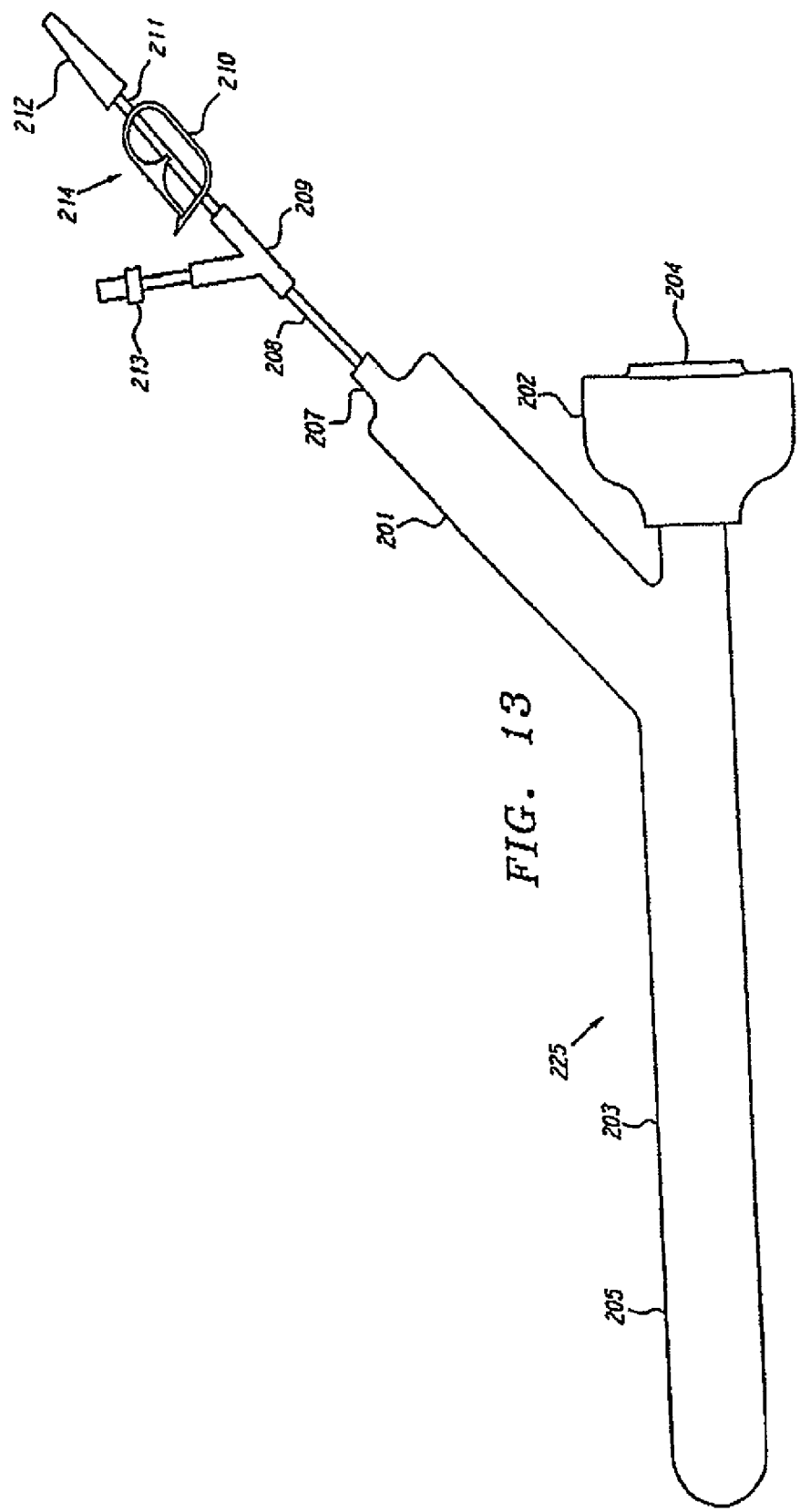
FIG. 13 is a plan view of the apparatus of FIG. 12 showing the elongate balloon fully distended after inflation.

Turning now to FIGS. 12 and 13, another embodiment of an extraluminal balloon dissection apparatus 223 according to the invention is disclosed. FIG. 12 illustrates the apparatus 225 as it would appear prior to use with the elongate balloon 203 inverted, folded and stored within balloon reservoir 201. FIG. 13 illustrates the apparatus 225 after the balloon 203 has been inflated and fully distended. The apparatus 225 is identical to the previous apparatus 200 except that the balloon sleeve 206 has been omitted and the inflation harness 214 has been relocated from the side of the balloon 203 to the reservoir 201. In this regard, it should be noted that the inflation harness 214 in the embodiment of FIGS. 10 and 11 could also extend from the reservoir 201.

Use of the apparatus 225 is likewise identical to use of the apparatus 200, with the exception that a laparoscope (not shown) is preferably utilized to guide the apparatus 225 into the incision and to advance the apparatus 225 to a point adjacent the elongate structure to be dissected. The surgeon may also manually insert the apparatus 225 into the incision adjacent the elongate structure without the aid of a laparoscope.

If observation is desired, the laparoscope is inserted through the seal 204 in the housing 202 and may be advanced distally into the reservoir 201 following the withdrawal of the folded balloon 203 from the reservoir 201. As continued inflation causes the folded balloon 203 to propagate, distally, the portion of the balloon 203 stored in the reservoir 201 is withdrawn and the laparoscope may be further advanced inside the interior space of the distended balloon 203 as desired. The flexible apparatus 225 allows the insertion angle of the laparoscope to be easily adjusted to parallel the structure being dissected.

Figure 14:
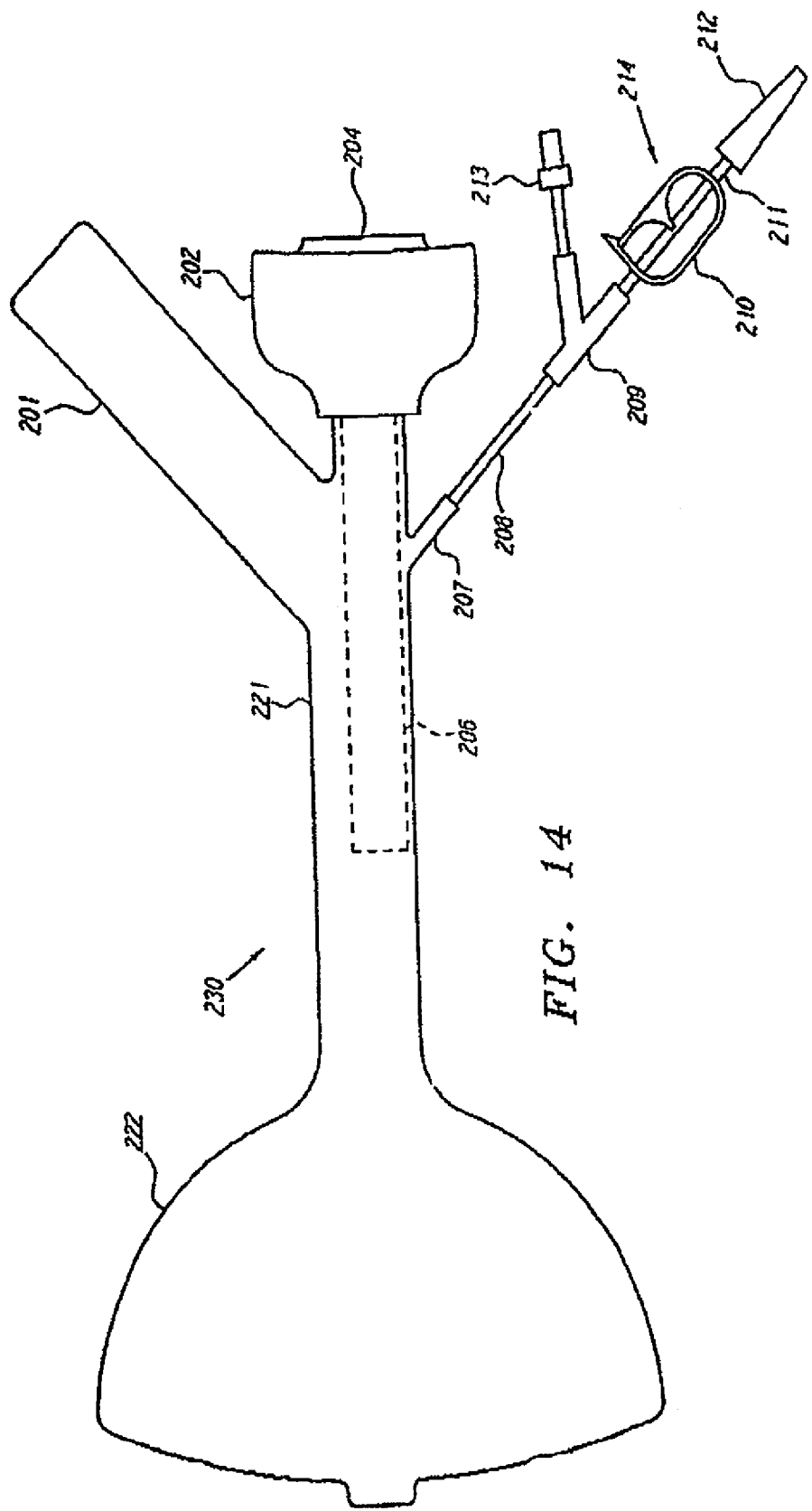
FIG. 14 is a plan view of another embodiment of an extraluminal balloon dissection apparatus according to the invention utilizing a balloon reservoir and a bulb-shaped balloon.
Figure 15:
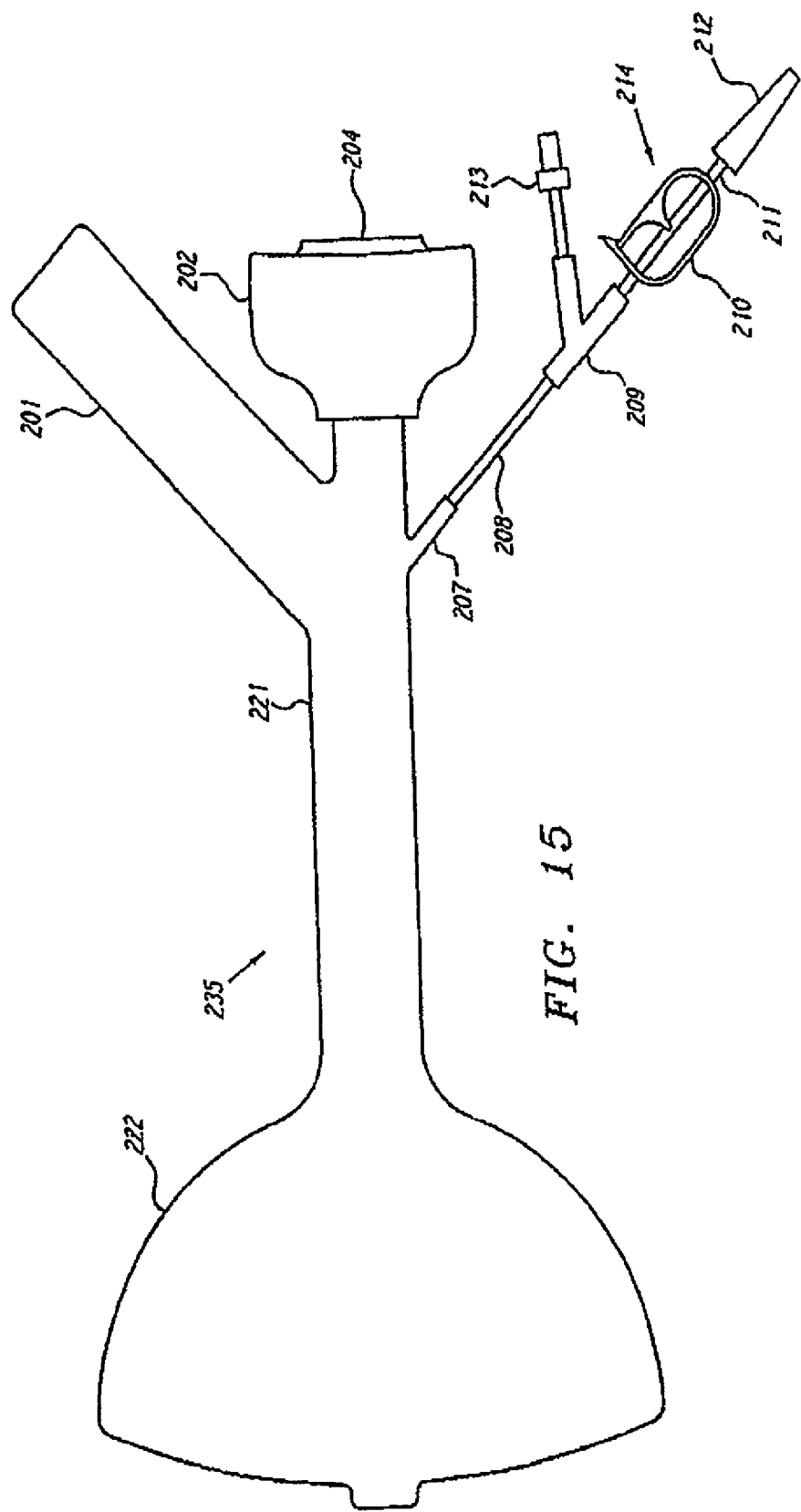
FIG. 15 is a plan view of yet another embodiment of an extraluminal balloon dissection apparatus according to the invention utilizing a balloon reservoir and a bulb-shaped balloon.

In FIG. 14, an extraluminal balloon apparatus 230 has bulb-shaped balloon 222 with an elongate neck which may be utilized in place of the elongate hot dog shaped balloon 203 of the apparatus illustrated in FIGS. 10 and 11. Similarly, FIG. 15 illustrates an apparatus 235 having a bulb-shaped balloon 222 with an elongate neck 221 in place of the elongate balloon 203 in the apparatus of FIGS. 12 and 13. Other than the shape of the balloon 222, the embodiments of the invention illustrated in FIGS. 14 and 15 are identical to their counterpart elongate balloon 203 embodiments illustrated in FIGS. 10 and 11 and FIGS. 12 and 13, respectively.

The balloon 222 utilized in the FIGS. 14 and 15 embodiments has a wide surface area distal portion which may be shaped as illustrated, or in any one of the shapes illustrated in application Ser. No. 08/570,766, for example. An elongate neck 221 extends from the distal portion of the balloon 222 and may be terminated within the housing 202 or on the balloon sleeve 206 (if utilized) as previously described. The deflated balloon 222 may be inverted inwardly, and the outer margins of the distal portion of the balloon 222 wrapped or folded together to compact and shorten the balloon 222. The inwardly folded and wrapped balloon 222 may then be pushed inside the balloon reservoir 201, as in previous embodiments.

When the balloon 222 is inflated, it will evert and propagate distally in a similar manner to that of the elongate balloon 203 of the previous embodiments. When the balloon 222 is essentially fully everted, the side margins of the distal portion of the balloon 222 will unroll, and the distal portion of the balloon 222 will fully expand. The balloon 222 may be used either as a dissector or as retractor, depending on the application. One application where the balloon 222 has been found to have particular utility is in connection with an aortic bifemoral bypass procedure, where either apparatus 230 or 235 may be inserted into the femoral canal of the patient and then inflated to cause the balloon 222 to dissect and retract the peritoneum from the pelvic floor.

Figure 16:
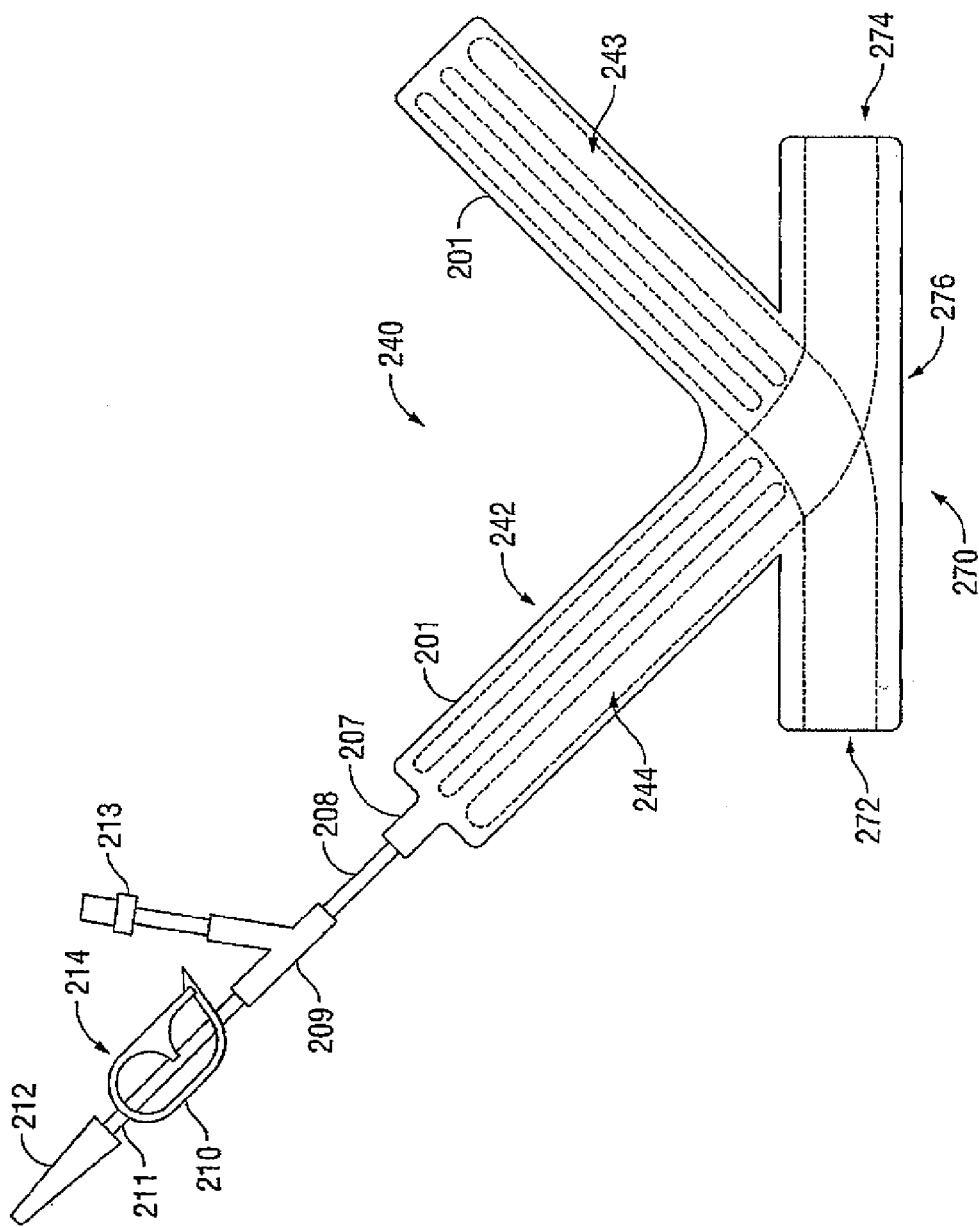
FIG. 16 is a side elevational view of another embodiment of an extraluminal balloon dissection apparatus according to the invention having two balloon reservoirs and a bi-directionally expanding elongate balloon.
Figure 17:
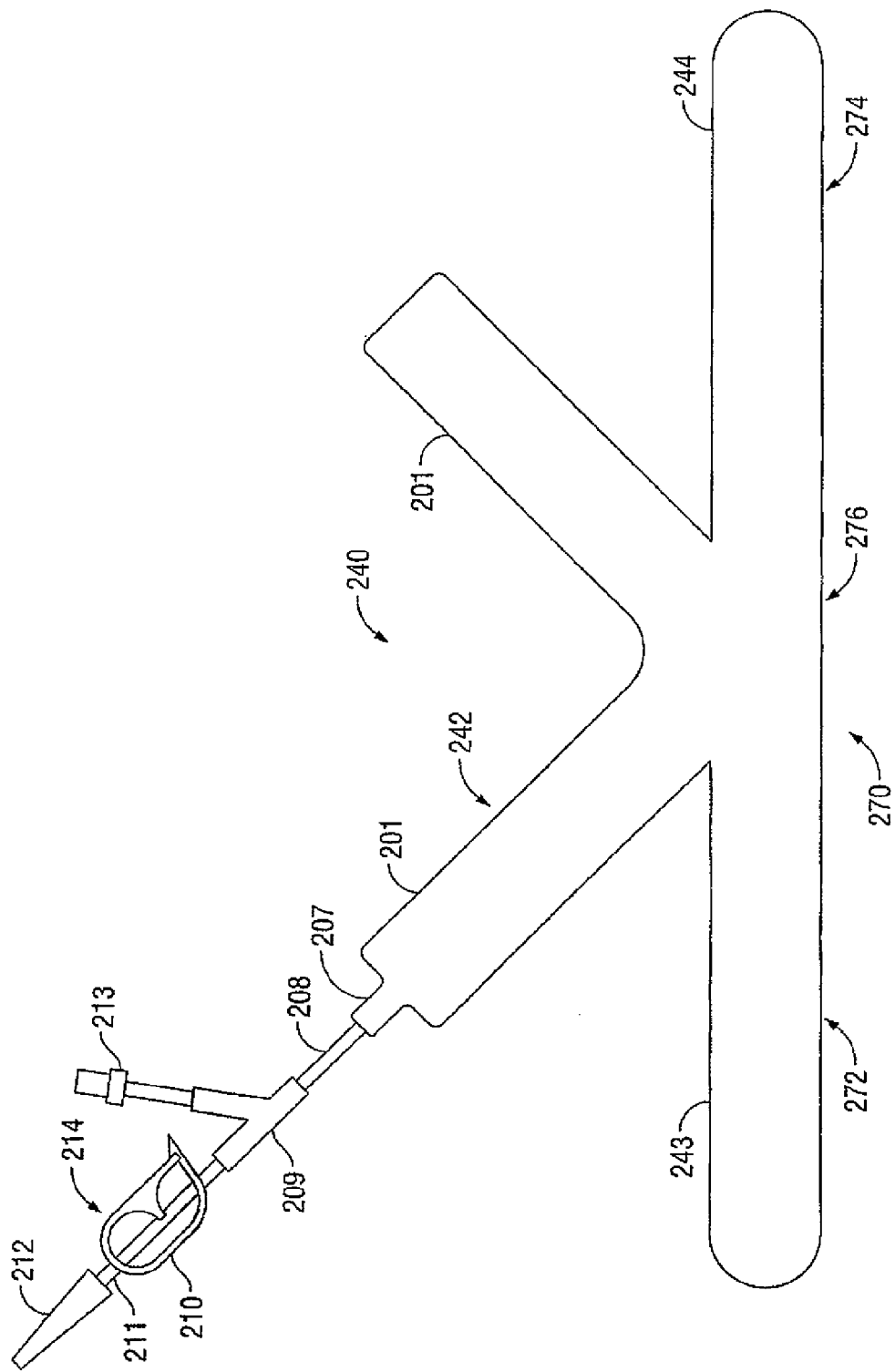
FIG. 17 is a side elevational view of the FIG. 16 embodiment illustrating the apparatus after the bi-directionally expanding balloon has been inflated and is fully distended.

FIGS. 16 and 17 illustrate a bi-directional extraluminal balloon dissection apparatus 240 which is provided with two integrally formed balloon reservoirs 201, each of which function to store approximately one-half of the bi-directionally expanding elongate balloon 242. The balloon 242 has a left portion 243 and a right portion 244, as shown packed in the reservoir 201 in the deflated predeployment state in FIG. 16 and in the fully expanded distended state in FIG. 17. The respective right 244 and left 243 halves of the elongate balloon 242 may be inverted inwardly and folded in the manner previously described. Each respective half of the folded elongate balloon 242 is then pushed into the opposite reservoir 201. A balloon inflation harness 214 of the type utilized in the previous embodiments may be utilized to inflate the balloon 242 and may be located on either one of the balloon reservoirs 201 or at some other point on the balloon 242.

The method of using the apparatus 240 is substantially similar to the methods of use previously described with regard to the prior embodiments. The apparatus 240 is inserted through an incision adjacent to elongate structure, and the balloon 242 is inflated. The right 244 and left 243 halves of the balloon 242 may be deployed simultaneously or sequentially, as desired. In practice, the right 244 and left 243 halves of the balloon 242 can be made to deploy sequentially by manually or otherwise impeding from unfolding one of balloon halves while the outer half is permitted to unfold. After the first half has unfolded and fully distended, the manual restraint may be released to deploy the other half. Each half of the balloon 242 everts and propagates distally with the folded balloon halves withdrawing from the reservoir 201 as the balloon halves propagate in the manner previously described.

A practical use of the apparatus 240 illustrated in FIGS. 16 and 17 is where it is desirable to avoid an anatomical structure that lies in the desired dissection path if a single entry point were utilized; or a structure which might impede dissection. Alternatively, the apparatus 240 may be utilized where it is desired to make an incision approximately at the midpoint of the portion of the elongate structure to be dissected and then to dissect the structure away from adjacent tissue in both axial directions. One example of a location where it may be desirable to utilize the bi-directional balloon 242 is the knee, where anatomical structures within the knee may preclude, or make difficult, use of an apparatus in which the dissecting balloon only expands in one direction. The balloon 242 can be inserted through an incision adjacent a blocking anatomic structure, and inflated to cause the balloon halves to propagate in opposite axial directions alongside an elongate structure, thereby avoiding the blocking structure.

Figure 18:
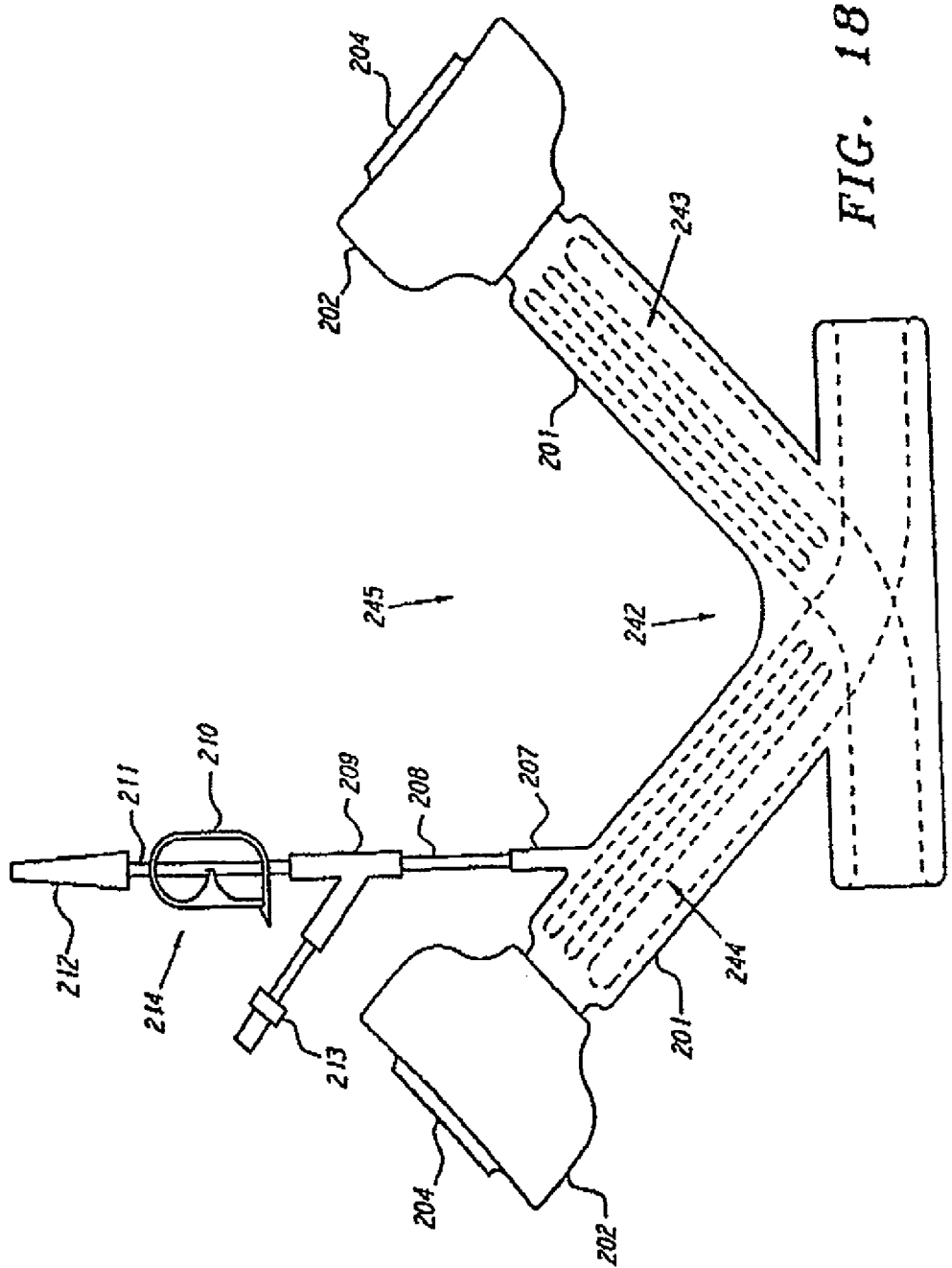
FIG. 18 is a side elevational view of another embodiment of an extraluminal balloon dissection apparatus according to the invention which is substantially similar to the embodiment of FIG. 16 which provides for laparoscopic observation.
Figure 19:
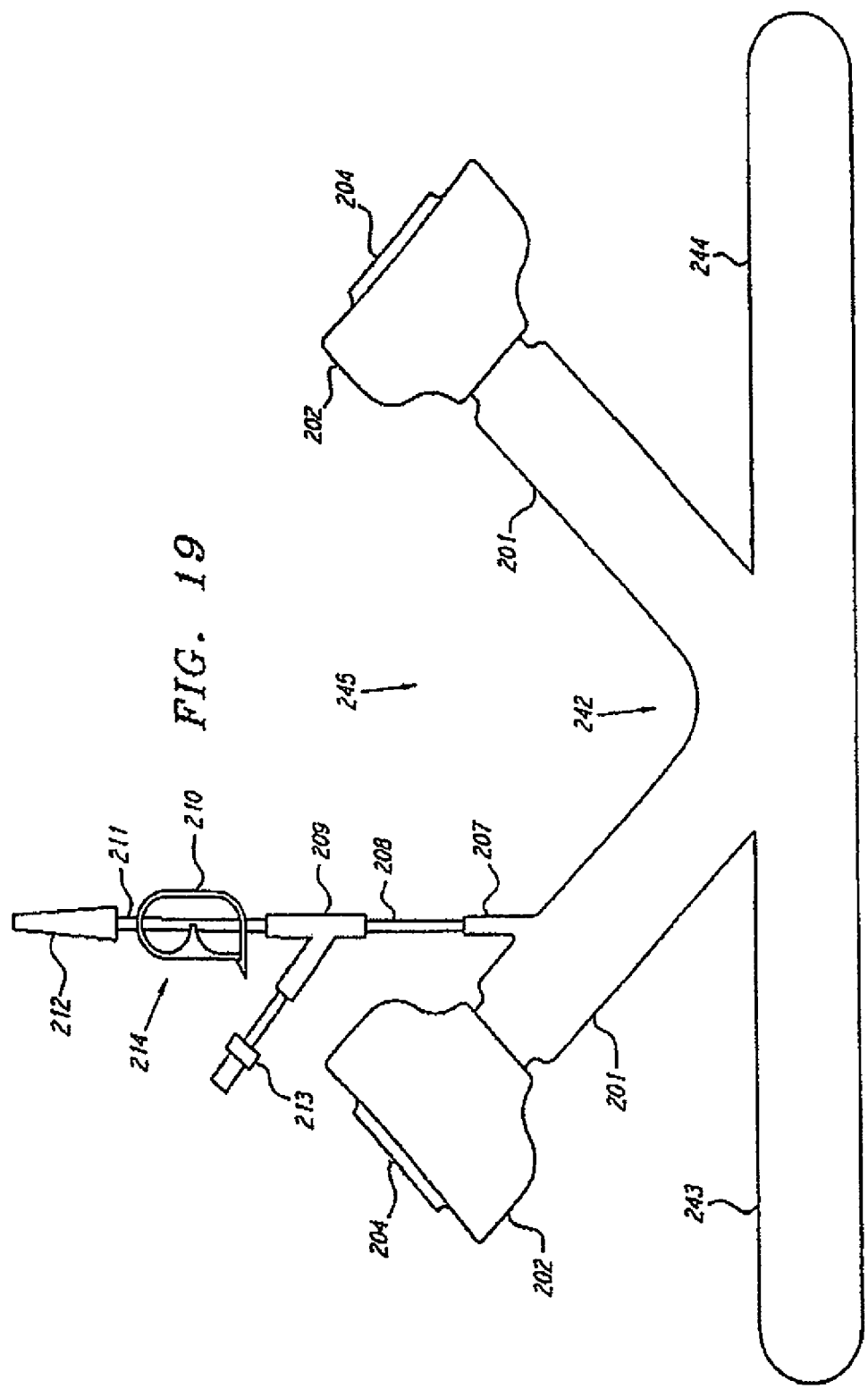
FIG. 19 is a side elevational view of the FIG. 18 embodiment after the bi-directionally expanding balloon has been inflated and is fully distended.

FIGS. 18 and 19 illustrate a variation on the apparatus 240 illustrated in FIGS. 16 and 17. The extraluminal balloon dissection apparatus of FIGS. 18 and 19 differs from the apparatus 240, only in that housings 202 having instrument seals 204 are provided to receive a laparoscope. The housings 202 and seals 204 are as previously described and are mounted on the balloon reservoirs 201 which are open-ended in this embodiment. The open-ended balloon reservoirs 201 may be secured within the housing 202 in a fluid-tight arrangement, as previously described. The addition of housing 202 to the apparatus 245 permits a laparoscope (not showing) to be inserted through the instrument seal 204 and the housing 202 into the interior space of the balloon 242. After the device 245 has been inserted through an incision in the body adjacent the elongate structure by use of a finger or other aid, the elongate bi-directional balloon 242 is inflated to dissect tissue adjacent elongate structure, starting from the middle of the structure and thereafter propagating axially in two different directions. (See FIG. 19) As the balloon 242 is inflated, a laparoscope may be inserted through the housing 202 having the instrument seal 204 and advanced following the balloon 242 alongside the structure being dissected. In order to advance the laparoscope into the balloon 242, it may be necessary to bend the housing 202 and reservoir 201 slightly to align the laparoscope with the axis of the everting balloon 242 as it dissects alongside the structure.

Figure 20:
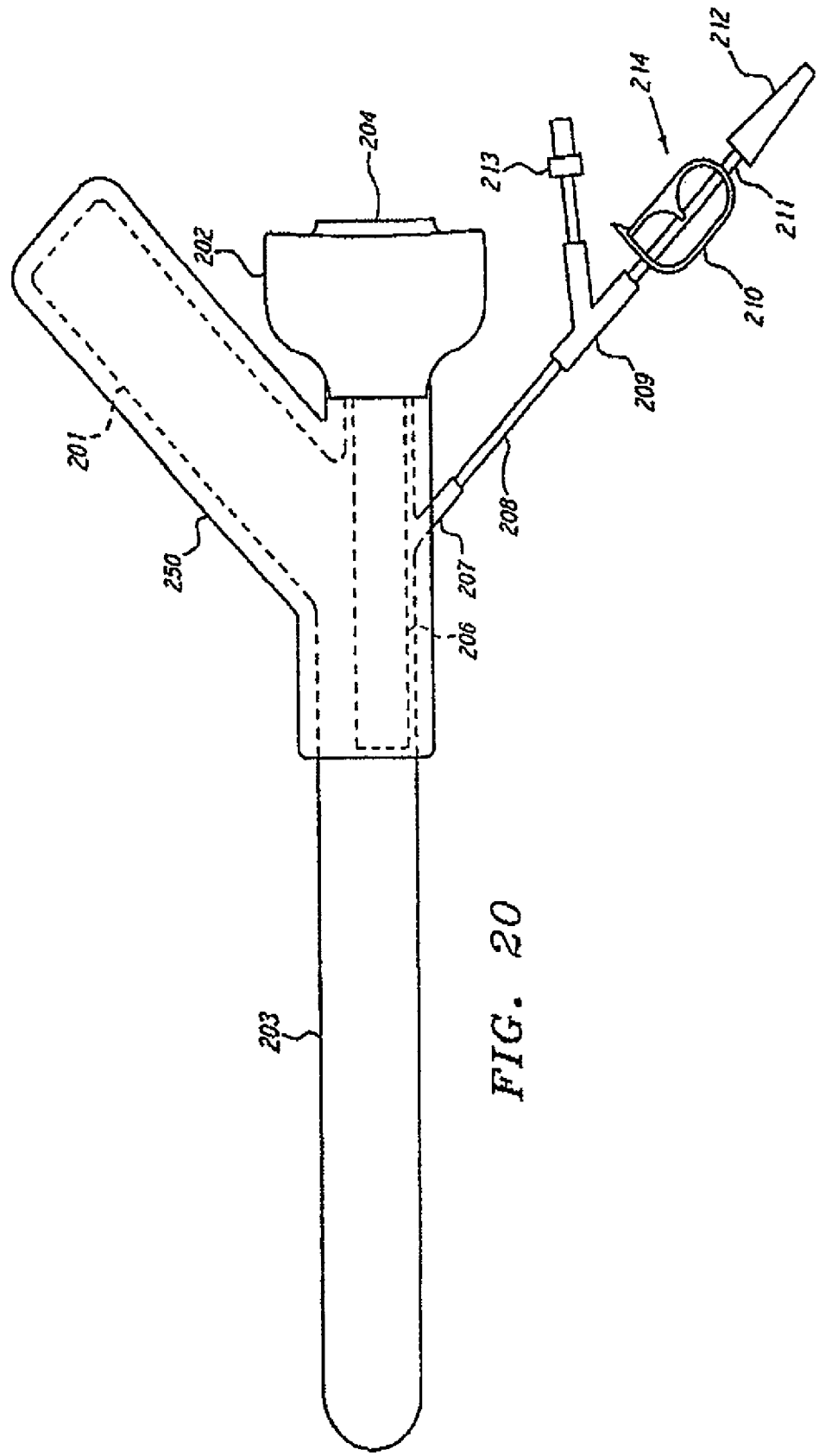
FIG. 20 is a plan view of a balloon reinforcing sleeve which may be utilized with an extraluminal balloon dissection apparatus in accordance with the invention.

FIG. 20 illustrates the use of a reinforcing glove or sheath 250 which may be utilized to reinforce the region of the balloon 203 around the balloon reservoir 201. The reinforcing sleeve 250 may also extend distally of the reservoir 201, as shown in FIG. 20. Although the use of a reinforcing sleeve 250 is illustrated in FIG. 20 in connection with the extraluminal balloon dissection apparatus 200 previously described with reference to FIGS. 10 and 11, it should be appreciated that the reinforcing sleeve 250 could be utilised in connection with any of the embodiments having a balloon reservoir, or otherwise where it is desired to reinforce a portion of a balloon. The reinforcing sleeve 250 may be formed of the same material as the elongate balloon 203 and mounted such that it surrounds the reservoir 201 and the portion of the elongate balloon 203 into which the balloon sleeve 206 extends. The reinforcing glove 250 may be formed from a flat sheet or sheets of material and may optionally be bonded to the reservoir 201. Alternatively, a reinforced monolithic structure may be used. The function of the reinforcing sleeve 250 is to reinforce any weak spots on a balloon that may occur, on the reservoir 201 for example, or alternatively, to reinforce a weak spot on a balloon that may occur within the body. Such weak spots may be caused by manufacturing variations in the balloon or by tissue differences within the body and, without reinforcement, may be manifested in balloon aneurism behavior.

From the foregoing, it can be seen that the balloon dissection apparatus and methods disclosed hereto are particularly suitable for the treatment of elongate structures, such as vessels, using extraluminal procedures. Extraluminal balloon dissection as disclosed herein has a wide variety of applications where it is desired to dissect alongside an elongate structure to create an anatomic working space exposing the structure. The procedures contemplated herein are minimally invasive in that small incisions are utilized and body tissue is minimally disrupted. Because dissection is along a naturally occurring tissue plane adjacent the elongate structure, bleeding is minimized and the time required for healing is reduced. Other patient advantages offered by extraluminal balloon dissection include marked reductions in recovery time and post-surgery pain over traditional open procedures.

Having thus described an embodiment of the invention, it will now be appreciated that the objects of the invention have been fully achieved, and it will be understood by one skilled in the art that many changes in construction and widely differing embodiments and applications of the invention will suggest themselves without departing from the spirit and scope of the invention. Accordingly, the written description provided herein is purely demonstrative and is not intended to be in any sense limiting.

The invention claimed is:

1. An apparatus for creating an anatomic working space, the apparatus comprising:
   first and second reservoirs; and
   a balloon transitionable between inflated and deflated states, the balloon including a first portion disposed within the first reservoir in the deflated state and a second portion disposed within the second reservoir in the deflated state, wherein in the inflated state, the first portion extends in a first direction and the second portion extends in a second direction, thereby defining an elongate portion of the balloon.

2. The apparatus according to claim 1, wherein the elongate portion is substantially linear.

3. The apparatus according to claim 2, wherein the balloon is formed of a non-elastomeric material.

4. The apparatus according to claim 3, wherein the balloon is formed of a substantially transparent material.

5. The apparatus according to claim 4, further comprising an inflation harness for introducing an inflation fluid into the balloon.

6. The apparatus according to claim 5, wherein the inflation harness is coupled to at least one of the first and second portions of the balloon.

7. The apparatus according to claim 1, further comprising a housing having a seal disposed therein, the seal providing a substantially fluid tight seal between a lumen of the housing and a surgical instrument inserted into the lumen.

8. The apparatus according to claim 7, wherein the housing is attached to a proximal end of at least one of the first and second reservoirs.

9. The apparatus according to claim 1, wherein at least one of the first and second portions of the balloon is configured to be inwardly foldable.

10. The apparatus according to claim 1, wherein the first and the second reservoirs are integrally formed.

11. The apparatus according to claim 1, wherein the balloon is a bi-directionally expandable balloon.

12. The apparatus according to claim 11, wherein the first and second reservoirs define an acute angle therebetween.

* * * * *